United States Patent [19]

Kapralis et al.

[11] Patent Number: 4,460,546
[45] Date of Patent: Jul. 17, 1984

[54] TRIGGER TO CONTROLLABLY INITIATE CRYSTALLIZATION

[76] Inventors: Imants P. Kapralis, 3020 S. Punta Del Este Dr., Hacienda Heights, Calif. 91745; Harry Krukle, 7023 Bevis Ave., Van Nuys, Calif. 91405

[21] Appl. No.: 177,258

[22] Filed: Aug. 11, 1980

[51] Int. Cl.³ ............................................. B01D 9/02
[52] U.S. Cl. .................................. 422/245; 126/263
[58] Field of Search ............... 23/301; 62/4; 126/263; 165/46, 63, 64, DIG. 4; 44/3 R; 428/596; 422/245, 254; 252/70

[56] References Cited

U.S. PATENT DOCUMENTS

| | | | |
|---|---|---|---|
| 811,750 | 2/1906 | Spieske | 252/70 |
| 1,502,744 | 7/1924 | Perrault | 44/3 A |
| 1,656,366 | 1/1928 | Sterling | 44/3 A |
| 1,679,432 | 8/1928 | Lyon | 44/3 B |
| 1,894,775 | 1/1933 | Levenson | 252/70 |
| 2,157,169 | 5/1939 | Foster | 126/263 |
| 2,220,777 | 11/1940 | Othmer | 126/263 |
| 2,827,438 | 3/1958 | Broadley | 252/70 |
| 3,093,308 | 6/1963 | Snelling | 236/1 |
| 3,175,558 | 3/1965 | Caillouette et al. | 128/403 |
| 3,223,081 | 12/1965 | Hunt | 126/360 R |
| 3,468,025 | 9/1969 | Messinger | 428/596 |
| 3,475,239 | 10/1969 | Fearon et al. | 44/3 R |
| 3,536,058 | 10/1970 | Hearst | 126/204 |
| 3,550,578 | 12/1970 | Fearon | 126/263 |
| 3,854,156 | 12/1974 | Williams | 126/204 |
| 3,951,127 | 4/1976 | Watson et al. | 126/206 |
| 4,077,390 | 3/1978 | Stanley et al. | 23/301 |
| 4,379,448 | 4/1983 | Kapralis et al. | 126/263 |

Primary Examiner—Hiram H. Bernstein
Attorney, Agent, or Firm—William W. Haefliger

[57] ABSTRACT

A trigger usable in initiating crystallization of a supercooled salt solution comprises a thin metallic strip containing multiple pin-hole size openings, and which is bendable with snap displacement. The strip may typically be non-ferrous.

9 Claims, 8 Drawing Figures

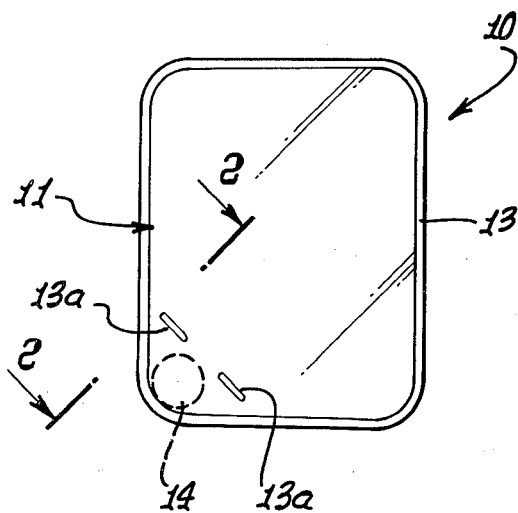
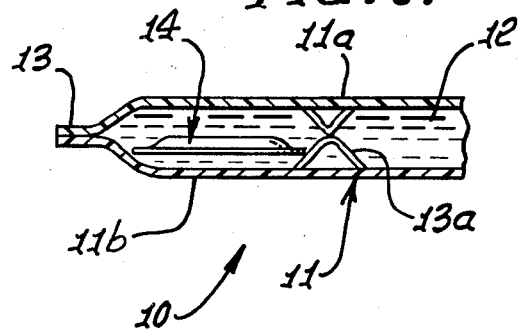
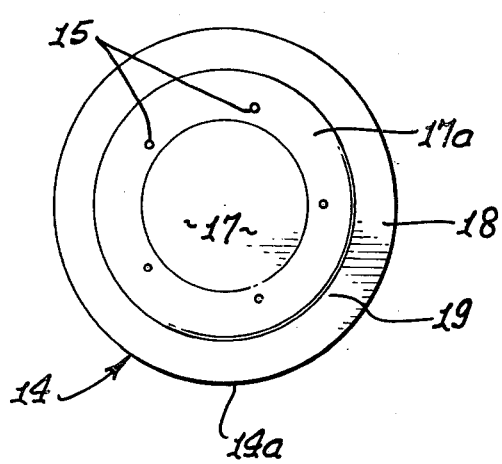
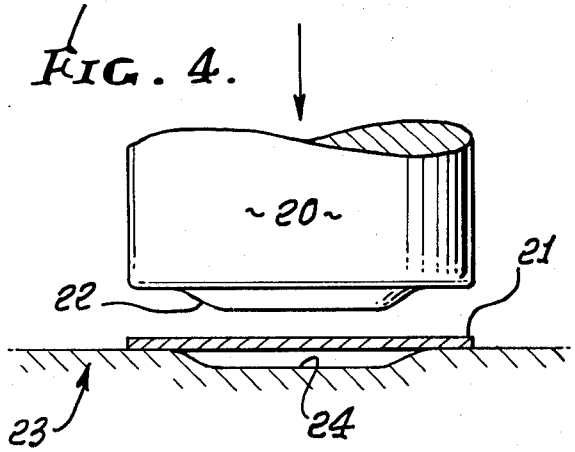
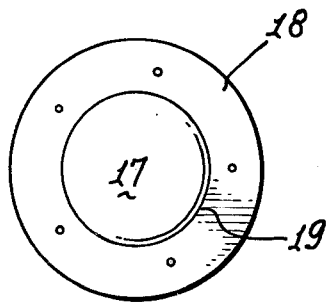
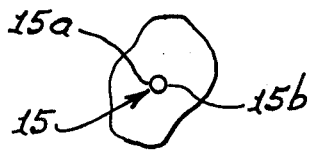
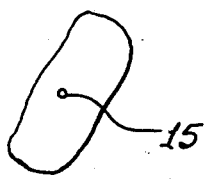

TRIGGER TO CONTROLLABLY INITIATE CRYSTALLIZATION

BACKGROUND OF THE INVENTION

This invention relates generally to the initiation of crystallization of a supercooled salt solution; more particularly it concerns the provision of a highly advantageous trigger that is easily deformable and is constructed to initiate such crystallation when the trigger is deformed, and without failure or injury to a plastic container in which the trigger is confined.

Devices of the general type with which the present invention is concerned are described in U.S. Pat. No. 4,077,390; however, such devices have tended to suffer from unreliable triggering of crystallization. For example, flexing of the actuator strips described in that patent at times will initiate crystallization and at other times will not. This greatly aggravates the user and reduces the practicality and utility of such devices. Also, the ferrous trigger of the patent can corrode.

SUMMARY OF THE INVENTION

It is a major object of the present invention to provide an improved trigger which will reliably and repeatedly produce or initiate crystallization of supercooled solutions; which is readily produced; and which will not injure or tear the plastic container in which it is incorporated. Fundamentally, the trigger comprises:

(a) a thin non-ferrous strip having a perimeter, (b) the strip having a multiplicity of openings formed therein, each opening characterized as having opposed edges which face one another in near touching relation, (c) the strip further characterized as having two configurations between which it is bendable with snap-displacement causing the edges to initiate progressive exothermic crystallization of said salt in the solution.

As will appear, the openings are generally circular or oval, and are sufficiently small that their edges may rub against one another and compress the solution trapped between those edges when the trigger is snap-deformed; the trigger is typically formed as a disc wherein the openings are spaced inwardly from the boundary or periphery of the disc; the disc typically has a dished central portion free of openings and adapted to "oil can" or snap "over center" when the disc is subjected to flexing or bending; and the disc or strip metal is typically impacted during fabrication to impact orient the molecular structure so as to aid the functioning of the disc or strip to produce or initiate crystallization. The strip typically consists of phosphor bronze or beryllium copper.

These and other objects and advantages of the invention, as well as the details of an illustrative embodiment, will be more fully understood from the following description and drawings, in which:

DRAWING DESCRIPTION

FIG. 1 is a plan view of a device incorporating the invention;

FIG. 2 is an enlarged section taken on lines 2—2 of FIG. 1, and showing a trigger in one side elevation configuration;

FIG. 2a is a side elevation showing the FIG. 2 trigger in a second side elevation configuration, i.e. after snap-displacement;

FIG. 3 is a further enlarged plan view of the trigger seen in FIG. 2;

FIG. 4 is a side elevation showing a step in the fabrication of the FIGS. 2 and 3 trigger;

FIG. 5a is a fragmentary plan view of an opening as initially formed in the trigger blank or strip;

FIG. 5b is a fragmentary plan view like FIG. 5a, but showing the opening after impacting as in FIG. 4;

FIG. 6 is a view like FIG. 3, showing a modified trigger.

DETAILED DESCRIPTION

Referring first to FIGS. 1 and 2, a flexible heat pack 10 includes a flexible plastic container 11 containing a supercooled solution 12, one example being aqueous sodium acetate as referred to in U.S. Pat. No. 4,077,390. The container may consist of translucent or transparent plastic, such as polyethylene or PVC. The upper and lower container walls 11a and 11b may be peripherally bonded or heat sealed together, as indicated at 13, whereby the solution 12 is contained against leakage.

Located in the container is a trigger 14 adapted to be deformed to initiate exothermic crystallization of the salt in the solution, and for that purpose the concentration of the salt is sufficient to produce such crystallization in response to trigger bending, as will be described. The trigger may be retained in the corner of the rectangular container by interruptedly bonded portions of the container walls, indicated at 13a, inwardly of peripheral bonding 13; at the same time, the solution has access to the trigger, at all times, via interruptions between bonded portions 13a. Other trigger locations are usable; or, the trigger may freely float.

Generally speaking, the trigger comprises a thin strip, (for example about 0.005 inches thick) such as a non-ferrous metallic disc, having a perimeter indicated at 14a in FIG. 3. Workable non-ferrous metals have been found to include phosphor bronze and beryllium copper. Phosphor bronze typically consists of about 80% copper, 10% tin, 9% antimony and 1% phosphorus. Beryllium copper is a copper alloy containing a small amount of beryllium and typically some nickel or cobalt. Perimeter 14a is free of sharp edges that could injure or penetrate the plastic walls 11a and 11b. The strip has a multiplicity of very small openings 15 formed therein, each opening or puncture characterized as having opposed edges which face one another in near touching relation. Typically, the openings initially formed in the strip are of pin-hole size. FIG. 5a shows a typical opening 15 as initially formed through the disc or strip, and with opposite elongated edges 15a and 15b. FIG. 5b shows an opening as it finally is formed or exists, with the edges 15a and 15b so close together that they do not appear distinct; however, there are slight gaps between and spaced along such edges, which may touch one another between the gaps.

The disc shaped strip 14 is characterized as having two configurations between which it is bendable with snap-displacement causing the described edges to initiate progressive exothermic crystallization of the salt in the supercooled solution in the container. Note for example the first stable configuration of the trigger strip 14 in FIG. 2, and its second (and relatively stable) curved configuration 14' in FIG. 2a. The user simply applies finger pressure on the container walls 11a and 11b snap-deforms the disc 14 to FIG. 2a configuration, in the container. This causes the edges 15a of the openings to actuate the crystallation, due to sudden deformation (as for example sudden local compression) of the solution trapped or confined in the spaces between the approximately touching edges. The snap-displacement of the nearly touching edges is found to initiate crystallation without failure or malfunction.

These purposes are served to unusual advantage by causing the disc to have dished configuration as in FIG. 2, so as to "oil-can" when deformed, i.e. easily snap over-center into FIG. 2a configuration. Further, the disc has a central portion 17 free of openings, and an outermost annular section 17a. The latter contains the openings, which are typically spaced inwardly from the perimeter 14a so that the latter is continuous, aiding the snap-displacement referred to. In FIGS. 2, 2a and 3, the openings are located in the outermost annular section 17a of the dished portion of the disc; whereas in FIG. 6, the openings are located in the undished outer annular portion 18. Circles 19 in FIGS. 3 and 6 generally designate the boundary between the dished and undished portions.

Finally, the performance of the disc shaped strip to initiate crystallization is aided by impact orientation of the molecular structure of the edges 15a. FIG. 4 shows a striker 20 being forcibly urged downwardly toward blank 21, after the latter has had tiny openings 15 formed therein as described. The bottom of the striker is protuberant at 22 to "dish" the blank (i.e. permanently deform it to have a central bulge as in FIG. 2); thereafter, the trigger disc is stamped or cut out of the blank by a suitable die. Back up platen 23 in FIG. 4 has a recess 24 to receive the deformed bulge of the blank 21.

We claim:

1. For use in initiating crystallization of a supercooled salt solution, the combination that includes a flexible container containing said solution, and a trigger located in the container in contact with the solution, the trigger comprising
    (a) a thin, non-ferrous, metallic strip having a perimeter,
    (b) said strip having a multiplicity of openings formed therein, each opening characterized as having opposed edges which face one another in near touching relation, said openings being of pin-hole size and everywhere spaced inwardly from the strip periphery,
    (c) the strip further characterized as having two configurations between which it is bendable with snap-displacement causing (said edges to initiate) progressive exothermic crystallization of said salt in the solution,
    (d) the strip being in the general form of a dished disc having a central portion and an outer portion surrounding said central portion, the outer portion having a curved periphery,
    (e) said openings everywhere spaced inwardly from the disc periphery and located in at least one of said disc portions whereby said periphery is free of opening edges which could otherwise penetrate the container, the container consisting of plastic material,
    (f) the strip having molecular structure which is impact oriented.

2. The trigger of claim 1 wherein said openings are generally circular.

3. The trigger of claim 1 wherein said strip is metallic and has dished configuration in one of said configurations characterized as stable.

4. The trigger of claim 1 wherein said opening are located in said outer portions.

5. The trigger of claim 1 wherein said strip consists of beryllium copper.

6. The trigger of claim 1 wherein said strip consists of phospor bronze.

7. The trigger of claim 1 wherein the strip is in the form of a disc.

8. For use in initiating crystallization of a supercooled salt solution, the combination that includes a flexible container containing said solution, and a trigger located in the container in contact with the solution, the trigger comprising
    (a) a thin non-ferrous metallic strip having a perimeter,
    (b) said strip having at least one pin-hole size opening formed therein and spaced inwardly from the strip periphery,
    (c) the strip metal selected from the group consisting of phosphor bronze and beryllium copper,
    (d) the strip further characterized as having two configurations between which it is bendable with snap-displacement causing progressive exothermic crystallization of said salt in the solution,
    (e) the strip being in the general form of a dished disc having a central portion and an outer portion surrounding said central portion, the outer portion having a curved periphery,
    (f) said opening or openings located in said outer portion and said central portion being substantially free of said opening or openings, said opening or openings everywhere spaced inwardly from the disc periphery whereby said periphery is free of opening edges which could otherwise penetrate the container, the container consisting of plastic material,
    (g) the strip having molecular structure which is impact oriented.

9. For use in initiating crystallization of a supercooled salt solution, the combination that includes a flexible container containing said solution, and a trigger located in the container in contact with the solution, the trigger comprising
    (a) a thin metallic strip having a perimeter,
    (b) said strip having a multiplicity of pin-hole size openings therethrough and everywhere spaced inwardly from the strip periphery,
    (c) the strip further characterized as having two configurations between which it is bendable with snap-displacement causing progressive exothermic crystallization of said salt in the solution,
    (d) the strip being in the general form of a dished disc having a central portion and an outer portion surrounding said centra portion, the outer portion having a curved periphery,
    (e) said openings everywhere spaced inwardly from the disc periphery and located in a zone extending about said central portion, whereby said periphery is free of opening edges which could otherwise penetrate the container, the container consisting of plastic material,
    (f) the strip having molecular structure which is impact oriented.

* * * * *